United States Patent [19]

Salvo

[11] Patent Number: 4,820,157

[45] Date of Patent: * Apr. 11, 1989

[54] DENTAL BRIDGE

[76] Inventor: Christopher A. Salvo, 656 King St., Port Chester, N.Y. 10573

[*] Notice: The portion of the term of this patent subsequent to Apr. 5, 2005 has been disclaimed.

[21] Appl. No.: 943,319

[22] Filed: Dec. 16, 1986

Related U.S. Application Data

[63] Continuation-in-part of Ser. No. 800,782, Nov. 22, 1985, Pat. No. 4,735,571.

[51] Int. Cl.$^4$ ............................................ A61C 13/225
[52] U.S. Cl. ...................................... 433/180; 433/215
[58] Field of Search ............... 433/180, 181, 182, 215, 433/9

[56] References Cited

U.S. PATENT DOCUMENTS

| | | | |
|---|---|---|---|
| 3,487,545 | 1/1970 | Weissman | 433/215 |
| 3,641,670 | 2/1972 | Karageorge | 433/180 |
| 4,100,678 | 7/1978 | Yatabe | 433/9 |
| 4,360,342 | 11/1982 | Salvo | 433/180 |
| 4,380,435 | 4/1983 | Raeder et al. | 433/180 |
| 4,431,417 | 2/1984 | Weissman | 433/182 |
| 4,433,960 | 2/1984 | Garito et al. | 433/215 |

Primary Examiner—John J. Wilson
Attorney, Agent, or Firm—Lowe, Price, LeBlanc, Becker & Shur

[57] ABSTRACT

A dental bridge is described consisting of at least one pontic and a small support bar. The pontic has a masio-distally oriented slot therethrough dimensioned to receive the bar. The bar is intended to be mounted in abutment teeth in a dental preparation also dimensioned to correspond to the cross sectional configuration of the bar. A plurality of pontics are provided so that a pontic most closely resembling the shape and shade of the lost tooth can be used, and the dentist can select the pontic and construct the bridge therefrom.

18 Claims, 2 Drawing Sheets

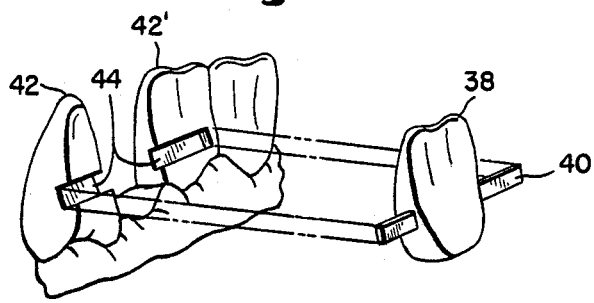
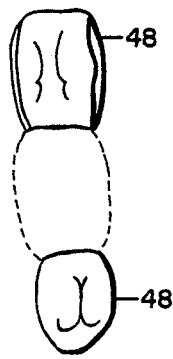 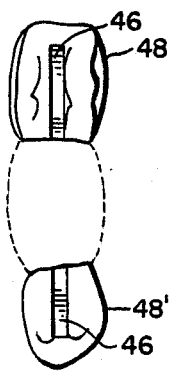 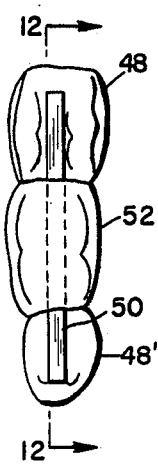 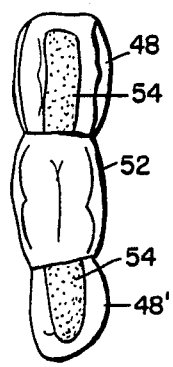
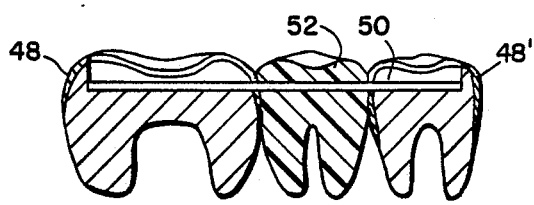
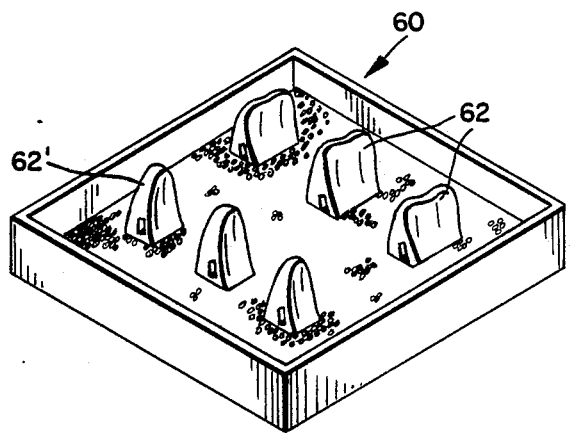

DENTAL BRIDGE

This application is a continuation-in-part of my U.S. patent application Ser. No. 800,782, filed Nov. 22, 1985, now U.S. Pat. No. 4,735,571, issued Apr. 5, 1988.

This invention relates to an improved dental bridge suitable for mass production and distribution in kit form so that it may be easily adapted to replacing one or more teeth whether the teeth are anterior, posterior, or both. The bridge of this invention is intended to provide individual pontics of varying sizes and shades so that the dentist may select replacement teeth which will match the patient's natural teeth. The bridge is also intended to be fitted easily and quickly without a massive restoration or removal or significant portions of abutment teeth.

In my prior U.S. Pat. No. 4,360,342 there is described a replacement dental bridge which consists of a bar or mesh support with one or more pontics mounted thereon. The support is intended to be fitted into a dental preparation one half to one millimeter deep in abutment teeth. The upper portion of the pontic including the occlusal surface is then intended to be prepared by the dentist, although the invention contemplates as an alternative a fully formed pontic tooth or teeth on the support. The support may be secured to the abutment teeth with a conventional bonding agent and/or pins.

In my co-pending application Ser. No. 800,782, filed Nov. 22, 1985, now U.S. Pat. No. 4,735,571, there is disclosed a dental splint for supporting mobile teeth. The splint is a bar preferably having cross sectional dimensions of one millimeter by two millimeters. A dental preparation is formed in one or more abutment teeth and in the mobile tooth or teeth and the bar secured by bonding and with pins which extend into the dentin of the teeth. This splint then is a means for supporting a mobile tooth without a massive removal or without the need to pull the tooth and replace it with a bridge.

In my also co-pending patent application Ser. No. 860,493 filed May 7, 1986, now U.S. Pat. No. 4,778,389, there is disclosed a novel stressless pin which can be used in a variety of dental applications including the dental splint above described or the dental bridge of my prior patent.

It has now been discovered however that a variety of different pontics can be provided to the dentist so that the dentist can select that most suitable to the individual patient and prepare a bridge. Preferably a bar of the above described invention is used to secure the pontic to abutment teeth. Each pontic is provided with a horizontal preferably mesio-distally oriented slot dimensioned to receive the bar running through the middle. Instead of a slot, the pontic may have a lingual, labial or gingival groove also dimensioned to receive the bar. A slot however is preferred. The slot may be lined with materials which permit attachment to the bar by any of a number of techniques such as by cementing, bonding with filled or unfilled resins, glues and other adhesives. The pontic may be fabricated in plastic, porcelain, metal, composites or other synthetic materials and the lining for the slot may be of the same or dissimilar material which will aid in strengthening the structure and/or aid in attachment.

The positioning of the slot in posterior teeth which have an occlusal surface is mesio-distally under the central groove of the tooth with the base of the slot preferably positioned occlusally at the juncture of the occlusal and middle thirds of the tooth where the contact area of the tooth is anatomically located. The slot is to run mesio-distally from distal contact area to mesial contact area.

The positioning of the slot in teeth which have a lingual surface (anterior teeth) is mesio-distally oriented and preferably located above the cingulum but centered just below or apical to the region of the contact area. This region is usually located at the juncture of the incisal and middle thirds of anterior teeth.

The bridge of this invention then may be supplied in kit form with an assortment in size, color and shape of pontic teeth which can be placed on the splint bar described above.

The disclosures of my above identified patent applications and my U.S. Pat. No. 4,360,342 are hereby incorporated by reference.

Accordingly it is an object of this invention to provide a dental bridge in which the dentist may select the pontic tooth or teeth from a variety of such teeth so that the pontic most closely matches or contrasts those of the patient, as desired.

It is another object of this invention to provide a dental bridge wherein the pontic tooth or teeth have mesio-distally oriented horizontal slots dimensioned to be fitted on a bar which then is secured to abutment teeth in a dental preparation without massive removal of abutment teeth material.

It is another object of this invention to provide a kit consisting of a plurality of pontic teeth, each tooth having a mesio-distally oriented horizontal slot dimensioned to fit on a splint bar which then is secured to abutment teeth in a dental preparation by cementing, bonding or the like.

It is still another object of this invention to provide a kit consisting of one or more dental splint bars and a plurality of pontic teeth, each tooth having a mesio-distally oriented horizontal slot therethrough with a lining adapted to bond to the bar so that when the pontic tooth is selected and fitted on the bar, a bridge will be formed which can then be mounted in dental preparation and abutment teeth without the need for massive removal of abutment teeth.

These and other objects will become readily apparent with reference to the drawings and following description wherein:

FIG. 7 is an exploded view showing placement of a bridge of this invention.

FIG. 8 is a top view showing placement of a pontic in phantom.

FIG. 9 is a view similar to FIG. 8 showing the dental preparation in abutment teeth.

FIG. 10 is a view similar to FIGS. 8 and 9 showing placement of the bridge in the dental preparation prior to filing.

FIG. 11 is a view similar to FIGS. 8, 9 and 10 showing placement of the bridge of this invention and filling the dental preparation.

FIG. 12 is a cross section view taken along lines 12—12 of FIG. 10.

FIG. 13 is a prospective view of a representation of a kit of this invention with a variety of different dental pontics.

Figure 1:
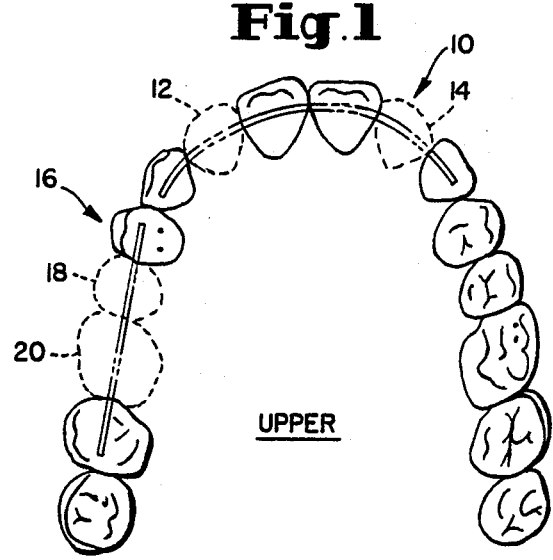
FIG. 1 is a representation of a human tooth structure having the bridge of this invention installed at four locations.
Figure 2:
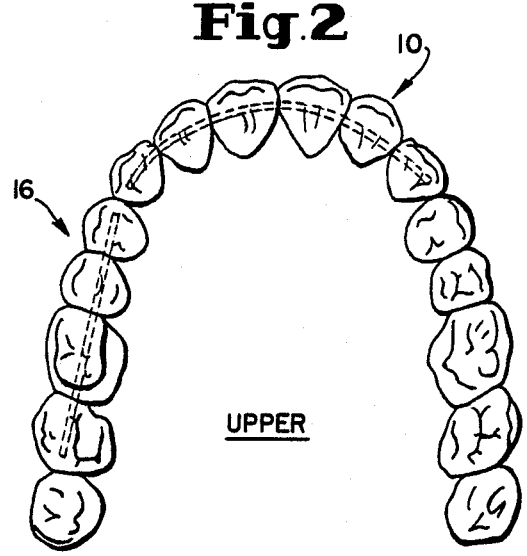
FIG. 2 is a representation similar to FIG. 1 after the bridge installation is complete.

With attention to the drawings, FIG. 1 illustrates different embodiments of the bridge of this invention after preparation and installation of the bridges but before the final filing step. FIG. 2 is the post operative appearance of the teeth of FIG. 1. FIG. 2 also conforms to the natural appearance.

With attention to FIG. 1, pontics are shown in phantom. The bridge 10 illustrates an anterior placement of pontics 12 and 14 wherein the bridge is anchored to abutment teeth at either end and at the center. The bridge 16 illustrates double pontics 18 and 20 with the bridge secured to abutment teeth at either end. The bridge 22 also mounts a pontic 24 and is secured at either end to abutment teeth. In contrast, the bridge 26 illustrates a double abutment with pontic 28 mounted at an end thereof. In the bridge at 10 both marginal ridges are removed from the incisors and only a single marginal ridge is removed from each of the cuspids. In the bridges at 16 and 22 likewise involve removal of a single marginal ridge from the abutment teeth. The bridge at 26 however entails the removal of both marginal ridges from the second bicuspid.

As shown in FIG. 1 also, the anterior bridge 10 involves a preparation on the lingual side of the front teeth. Bridges 16, 22 and 26 involve preparations on the occlusal surface of posterior teeth.

Figure 3:
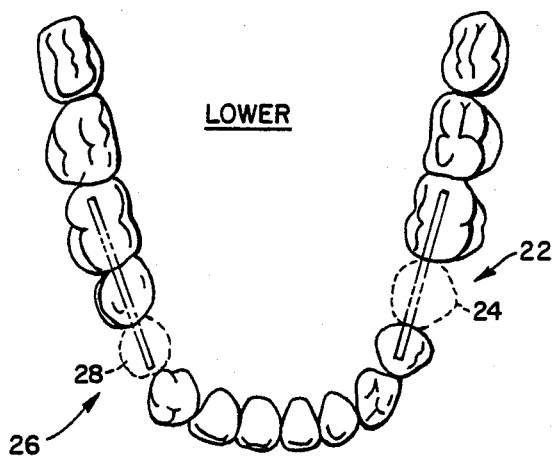
FIG. 3 is a front view of a anterior pontic tooth.
Figure 3:
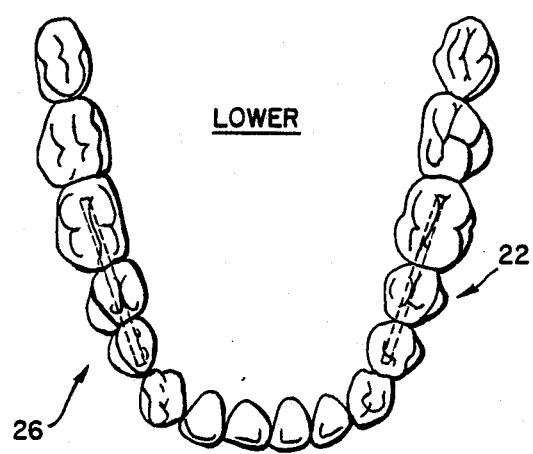
Figure 3:
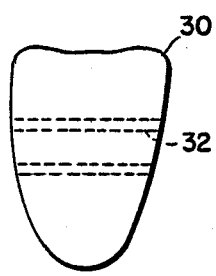
Figure 4:
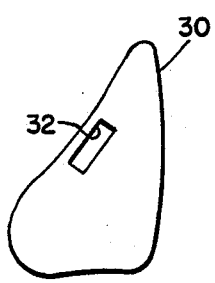
FIG. 4 is a side view of the tooth of FIG. 3.

With attention to FIGS. 3 and 4, there is pictured an anterior pontic tooth of this invention having a mesio-distally oriented slot 32 therethrough. The slot extends through the pontic tooth and is located preferably above the cingulum in the region of the contact area. This region is usually located at the juncture of the incisal and middle thirds of the anterior teeth. As will be subsequently explained, the slot 32 is dimensioned to receive a supporting bar and may be lined with a material which would facilitate attachment to the bar.

Figure 5:
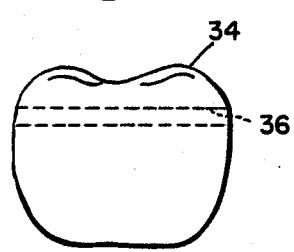
FIG. 5 is a side view of a posterior pontic tooth.
Figure 6:
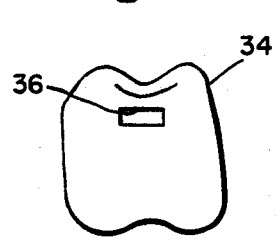
FIG. 6 is a front view of the pontic tooth of FIG. 5.

With attention to FIGS. 5 and 6 there is depicted a posterior pontic tooth 34 also having a mesio-distally oriented slot 36 therethrough. The positioning of slot 36 in posterior pontic tooth 34 is mesio-distally under the central groove of the occlusal surface of the tooth with the base of the slot being preferably positioned occlusally at the junction of the occlusal and middle thirds of the tooth where the contact area is anatomically located. The slot as shown runs from the distal contact area to the masial contact area.

Pontic teeth 30 and 34 may be fabricated in any conventional material including plastics, porcelain, metals, composites or other synthetics. The slots 32 and 36 may be lined with materials which permit attachment to the bar via a number of different techniques such as cementing, bonding with filled or unfilled resin, glues or other adhesives. The slot lining may be a similar or dissimilar material to that of the pontic tooth to add in strengthening the structure or the attachment to the bar as will be subsequently described.

With attention to FIG. 7, with reference to anterior teeth a pontic tooth 8 is mounted on a support bar 40 as shown by extending the bar through a slot similar to slot 32 shown in FIGS. 3 and 4 and attaching, rigidly the pontic 38 to the bar 40. The initial preparation involves removal of from 1 to ½ millimeter into dentin from abutment teeth 42 in the configuration of bar 40. The dental preparation 44 may involve removal of both marginal ridges from abutment teeth 42 and 42' but the most distant marginal ridge from edentulous area remains intact as shown.

With attention to FIGS. 8-12, in the case of posterior teeth a dental preparation 46 is prepared in the occlusal surface of abutment teeth 48 and 48' by removing to a depth of 1 millimeter to ½ millimeter apically or dentin in the configuration of the support bar 50. A pontic 52 which has a slot through it as shown in FIGS. 5 and 6, is mounted on the bar by extending the bar 50 through the pontic 52 and adhering the pontic rigidly thereto. The enamel is removed just past the junction the enamel and dentin so that bar 50 is supported against lateral movement Bar 50 may be the splint bar described in copending patent application Ser. No. 800,782, filed Nov. 22, 1985 and the disclosure which is incorporated by reference herein. The bar described in that application has a cross section dimension of about 1 millimeter by 2 millimeters and is provided with a number of holes for receiving dental pins or screws. A diameter of about 0.030 inches plus or minus 0.010 inch is acceptable for the holes. The apertures may be mutually spaced as described therein about one half millimeter apart and staggered. The bar may be constructed of metal or resin and preferably as a channel shape. The dental preparation 44 and 46 should extend only into the dentin and not into the pulp chamber. The bar is intended to be placed into the solid tooth structure. Similarly, if pins are used, the pins should extend only into the dentin.

The procedure for a preferred method for the dental bridge placement is as follows:

The operator should isolate the area into which he wishes to place the bridge. A rubber dam may be used and it is suggested wherever possible. The preparation either 44 or 46 is made on the lingual or occlusal surface. The preparation is then cleansed with a 3% peroxide solution. The enamel is etched and washed with water. It is preferred to coat the floor and walls of the preparation with an agent having strong bonding ability to both dentin and enamel. Examples of such agents are BONDLITE, or SCOTCHBOND as identified in my above referenced co-pending patent application.

Composite material is then placed on the floor of the preparation over the bonding agent. The composite material must have characteristics of total curing to its depth after light application is off because after the bar 50 or 40 is fitted in the preparation 46 or 44 the light will not fully penetrate beneath the bar. An example of such a material is Ultra Bond or Marathon composite material.

Bar 50 or 40 is then preferably cleansed with alcohol and/or 3% hydrogen peroxide. The fitted bar is then coated with the bonding agent and/or opaquer on all sides, cured and set aside in a clean area. An example of such an opaquer is Gold Link by Denmat.

The floor 42 of preparation 40 is cleansed with 3% hydrogen peroxide, dried and then coated with a thin layer of post exposure curable composite such as that manufactured by DEN-MAT.

A pontic tooth 52 or 48 is selected and mounted on the bar 50 or 40 as described above. The bridge is then placed snugly with the bar in the preparation and the bar is then covered with an opaque composite 54 and then layered over with a more filled composite. The bridge is then finished according to conventional fashion.

If pins (not shown) are to be used, the pins may be coated with the bonding agent. The pins are preferably cut to a workable length and inserted into holes previously drilled in the dentin through apertures (not shown) in the bar. The ends of the pins are then bent over preferably in the channel (not shown) provided in the bar. Upon completion of the procedure of this invention a rigid unitary bridge will be formed wherein the supporting bar is bonded to the tooth structure and the composite is also bonded both to the tooth structure, dentin and enamel and to the bar. The bridge then depends for seal on the bonded unitary mass and not on a composite mechanically gripping the bar and tooth structure. Strength is imparted by the rigid bar and the surrounding pontic tooth and bonded substance as well as intra-coronal dental preparations.

As shown in FIG. 13, a kit 60 may be provided for the dentist which includes a variety of pontics 62 and 62' which may be of different shades and shapes as desired. In this way the dentist can select the pontic most suitable for a particular patient and complete the preparation of the bridge and the operational procedure to mount the bridge in the patient's mouth in a very short time with minimal removal of tooth structure from abutment teeth.

This invention may be embodied in other specific forms without departing from the spirit or essential characteristics thereto. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. A method for providing a dental bridge to replace at least one missing tooth without substantial removal of portions of abutment teeth comprising the steps of:
   providing a substantially rigid bar member having a chemically reactive bondable surface;
   providing a plurality of dental pontics, each having an area therethrough dimensioned to receive said bar;
   selecting a dental pontic from said plurality of pontics most corresponding to the missing tooth;
   rigidly mounting said pontic on said bar by extending said bar through the slot therein;
   forming a dental preparation in the surfaces of said abutment teeth substantially conforming in cross sectional configuration to said bar and extending only into the dentin of said teeth, said preparation having a flat floor and walls perpendicular thereto;
   providing a filled resin composite material and a bonding agent for bonding said bar composite and tooth material;
   coating the walls and floor and the ends of said bar extending from said pontic with said bonding agent;
   coating the floor of said preparation with said composite;
   mounting said bar and said preparation on said composite coating; and
   covering said bar with said composite so that said composite, bar and teeth will be chemically bonded to form a unitary structure.

2. The method of claim 1 wherein the dimensioned area is a mesio-distally oriented slot extending through the pontic.

3. The method of claim 2 wherein the bar is non-metallic.

4. The method of claim 2 wherein said bar is metallic.

5. The method of claim 2 wherein the surface of said bar is roughened.

6. The method of claim 2 wherein the dental preparation is formed on the occlusal surfaces of said teeth.

7. The method of claim 2 wherein the dental preparation is formed on the lingual surfaces of said abutment teeth.

8. The method of claim 2 wherein said pontic is a posterior tooth and the slot is mesio-diatally oriented under the central groove positioned occlusally at the juncture of the occlusal and middle thirds of the tooth.

9. The method of claim 2 wherein the pontic is a anterior tooth and the slot is mesio-distally oriented above the cingulum at the juncture of the incisal and middle third thereof.

10. A method for providing a dental bridge to replace at least one missing tooth without substantial removal of portions of abutment teeth comprising the steps of:
    providing a substantially rigid bar member having a roughened bondable surface;
    providing a plurality of dental pontics, each having an area therethrough dimensioned to receive said bar;
    selecting a dental pontic from said plurality of pontics most corresponding to the missing tooth;
    rigidly mounting said pontic on said bar by extending said bar through the slot therein;
    forming a dental preparation in the surfaces of said abutment teeth substantially conforming in cross sectional configuration to said bar and extending only into the dentin of said teeth, said preparation having a flat floor and walls perpendicular thereto;
    providing a filled resin composite material and a bonding agent for bonding said bar, composite and tooth material;
    coating the walls and floor and the ends of said bar extending from said pontic with said bonding agent;
    coating the floor of said preparation with said composite;
    mounting said bar and said preparation on said composite coating; and
    covering said bar with said composite so that said composite, bar and teeth will be chemically bonded to form a unitary structure.

11. The method of claim 10 wherein the dimensioned area is a mesio-distally oriented slot extending through the pontic.

12. The method of claim 11 wherein the bar is non-metallic.

13. The method of claim 11 wherein said bar is metallic.

14. The method of claim 11 when the surface of said bar is chemically reactive.

15. The method of claim 11 wherein the dental preparation is formed on the occlusal surfaces of said teeth.

16. The method of claim 11 wherein the dental preparation is formed on the lingual surfaces of said abutment teeth.

17. The method of claim 11 wherein said pontic is a posterior tooth and the slot is mesio-distally oriented under the central groove positioned occlusally at the juncture of the occlusal and middle thirds of the tooth.

18. The method of claim 11 wherein the pontic is a anterior tooth and the slot is mesio-distally oriented above the cingulum at the juncture of the incisal and the middle third thereof.

* * * * *